(12) United States Patent  (10) Patent No.: US 8,454,488 B2
Hamel  (45) Date of Patent: Jun. 4, 2013

(54) SHIELDED HIGH DOSE RADIATION CATHETERS

(75) Inventor: Kory P. Hamel, Bloomington, MN (US)

(73) Assignee: AMS Research Corporation, Minnetonka, MN (US)

( * ) Notice: Subject to any disclaimer, the term of this patent is extended or adjusted under 35 U.S.C. 154(b) by 1684 days.

(21) Appl. No.: 11/828,174

(22) Filed: Jul. 25, 2007

(65) Prior Publication Data

US 2008/0027265 A1    Jan. 31, 2008

Related U.S. Application Data

(60) Provisional application No. 60/820,283, filed on Jul. 25, 2006.

(51) Int. Cl.
*A61N 5/00* (2006.01)
(52) U.S. Cl.
USPC ............................................................ 600/3
(58) Field of Classification Search
USPC ........................................................ 600/1–8
See application file for complete search history.

(56) References Cited

U.S. PATENT DOCUMENTS

| | | | |
|---|---|---|---|
| 6,033,357 A | 3/2000 | Ciezki et al. | |
| 6,309,339 B1 | 10/2001 | Ciezki et al. | |
| 6,416,492 B1 | 7/2002 | Nielson | |
| 6,626,816 B1 | 9/2003 | Ciezki et al. | |
| 7,686,755 B2 * | 3/2010 | Smith et al. | 600/3 |
| 2005/0027157 A1 * | 2/2005 | Winkler et al. | 600/3 |
| 2006/0100475 A1 * | 5/2006 | White et al. | 600/3 |

* cited by examiner

*Primary Examiner* — Christine Matthews
(74) *Attorney, Agent, or Firm* — Kimberly K. Baxter; Gregory L. Koeller

(57) ABSTRACT

An apparatus and method for tailoring the radiation intensity about a radiation source, enabling affected zones of a cancerous tissue mass to receive full radiation dosage while limiting the exposure of unaffected regions where radiation exposure is not desired. The assembly includes a radiation attenuator partially covering the outer periphery of a delivery portion of a high dosage radiation catheter, thereby altering the radiation profile that exits the assembly. A method for treating a cancer affected tissue mass includes inserting a plurality of said catheters into a tissue mass about the center of mass and orienting said catheter so that said the maximum radiation intensity is facing substantially toward the center of mass. The radiation source is allowed to dwell in the catheter for a prescribed period of time to deliver the desired dosage of radiation. The radiation source is then removed from the catheter.

7 Claims, 5 Drawing Sheets

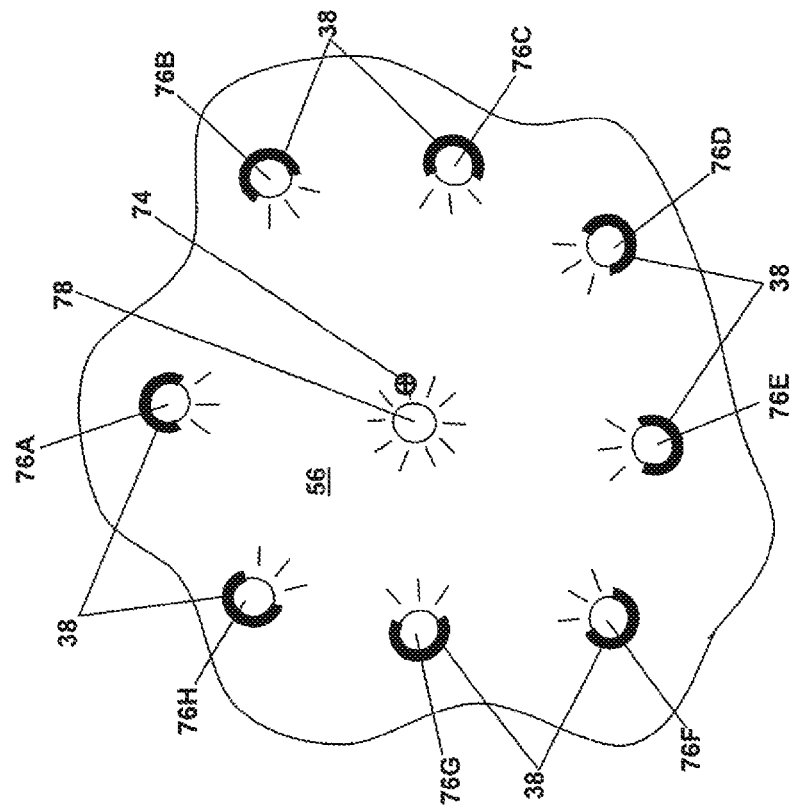
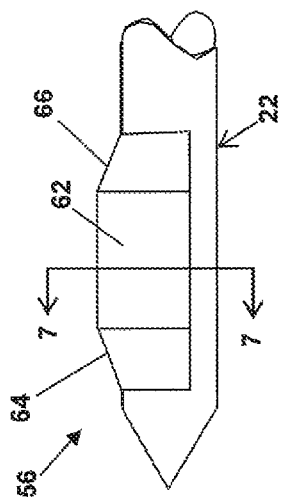
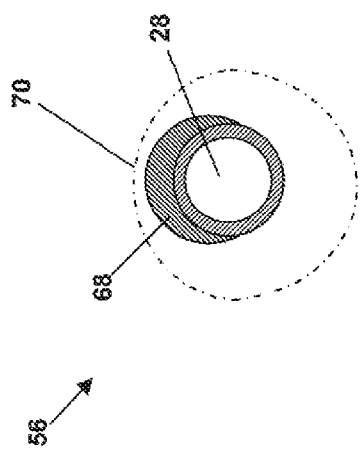

SHIELDED HIGH DOSE RADIATION CATHETERS

PRIORITY CLAIM

The present application claims priority to U.S. Provisional Application Ser. No. 60/820,283, filed Jul. 25, 2006 and entitled "SHIELDED HIGH DOSE RADIATION CATHETERS, which is herein incorporated by reference in its entirety.

FIELD OF THE INVENTION

The invention is directed generally to the field of catheters. More specifically, the invention is directed to catheters and methods utilized in high dose rate temporary brachytherapy.

BACKGROUND OF THE INVENTION

Brachytherapy is a form of internal radiation treatment where radioactive sources are placed on or within cancerous tumors. There are two major forms of brachytherapy: permanent seed implantation, wherein radioactive seeds are permanently placed within a cancerous gland or tissue mass, and high dose rate (HDR) temporary brachytherapy, which involves the temporary placement of a high intensity radiation source within or in close proximity to the cancerous tumor.

HDR temporary brachytherapy is particularly suited for treatment of prostate, gynecologic, breast, head and neck, lung, esophageal, bile duct, anorectal and sarcoma cancers. Tiny plastic catheters are placed in the subject tissue mass for administration of a series of radiation treatments. A computer-controlled machine, often referred to as an "afterloader," loads a highly radioactive seed, typically made of iridium, into each of the catheters in a serial fashion. The radiation dose delivered to a particular zone of the affected tissue mass may be tailored by altering the time the seed is allowed to dwell in a particular catheter—a significant advantage of HDR temporary brachytherapy over permanent seed implantation. The catheters are removed upon completion of the treatment series.

Minimization of exposure of certain regions of an affected tissue mass, as well as non-cancerous neighboring tissue, is typically desired during the HDR temporary brachytherapy. For example, in the treatment of prostate cancer, it is advantageous to minimize the exposure of the urethra and rectum during HDR treatment. Generally, directing the intensity of the radiation dose toward the cancerous tumor while reducing the intensity directed away from the tumor is desired.

SUMMARY OF THE INVENTION

An apparatus and method for tailoring the radiation intensity about a radiation source is disclosed. The apparatus and method enables the desired zones of the affected tissue mass to receive full radiation dosage while limiting the exposure of unaffected regions where radiation exposure is not desired. Embodiments of the invention thus permit increased intensities and dosages of radiation during a treatment session while mitigating damage to neighboring healthy tissues, thereby reducing the number of treatment sessions.

In one aspect, the present disclosure is directed to an HDR catheter apparatus comprising a hollow tubular element having a central axis and a distal end portion with an outer periphery, and a radiation source removably positioned in the distal end portion. A radiation attenuator partially covers the outer periphery of the distal end portion, defining a partially shrouded zone that alters the radial profile of the radiation intensity emitted by the radiation source. The uncovered portion of the outer periphery defines a window through which radiation passes relatively unattenuated. Other embodiments of the invention will be readily apparent to the skilled artisan.

In another aspect of the present disclosure, a method for treating a cancerous tissue includes selecting a plurality of the HDR catheters, each having a radiation attenuator that partially covers the outer periphery of a distal end portion, the uncovered portion of the outer periphery defining a window. Each of the HDR catheters are inserted into a region about the center of the cancerous tissue mass, and oriented so that the radiation window faces substantially towards the center of the cancerous tissue mass. A radiation source can then be routed through the hollow tubular element of one of the catheters and positioned within the partially shrouded zone at the distal end portion of the HDR catheter. The radiation source is allowed to dwell in the partially shrouded zone for a prescribed period of time to deliver the desired dosage of radiation to the affected zone of the cancerous tissue mass. The radiation source is then removed from the HDR catheter. The steps are repeated for each of the catheters in the tissue mass, with dwell times varying according to the dosage requirements. The method can further utilize one or more unattenuated catheters located near or within the center of mass of the cancerous tissue mass, or where the irradiation of neighboring zones is not a concern.

In still another aspect of this disclosure, a system for treating a cancerous tissue mass is described with an HDR catheter comprising a hollow tubular element having a central axis, a proximal end portion, a mid portion and a distal end portion with an outer periphery, and a radiation attenuator partially covering the outer periphery of the distal end portion. The radiation attenuator defines a partially shrouded zone of the distal end, and the uncovered portion includes a window portion. An afterloader including a radiation source is detachably connected to the proximal end of the HDR catheter. The proximal end of the HDR catheter is configured to receive the radiation source from the afterloader utilizing a drive wire that motivates the radiation source to or from the partially shrouded zone of the distal end portion through the proximal end portion and the mid portion.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

These as well as other objects and advantages of this invention, will be more completely understood and appreciated by referring to the following more detailed description of the presently preferred exemplary embodiments of the invention in conjunction with the accompanying drawings of which:

FIG. 6 depicts a distal end portion of an embodiment of an HDR catheter;

FIG. 7 is a cross-sectional view of the HDR catheter of FIG. 6 taken at line 7-7;

FIG. 8 is a cross-sectional view of a tissue mass under treatment of multifocal cancer according to an embodiment of the invention.

DETAILED DESCRIPTION OF EMBODIMENTS

Figure 1:
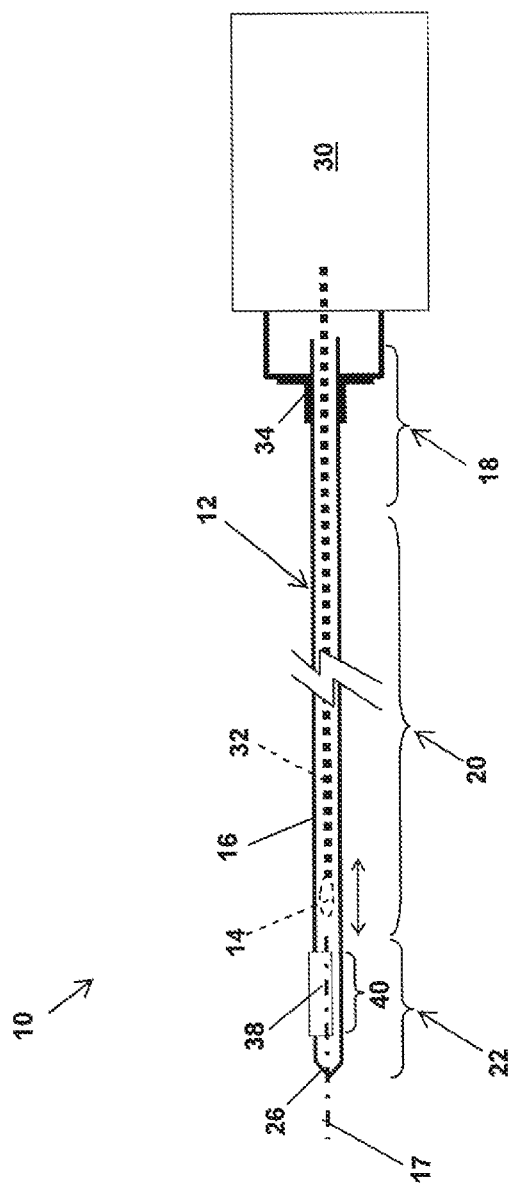
FIG. 1 depicts a temporary high dose radiation delivery system according to the present invention.
Figure 2:
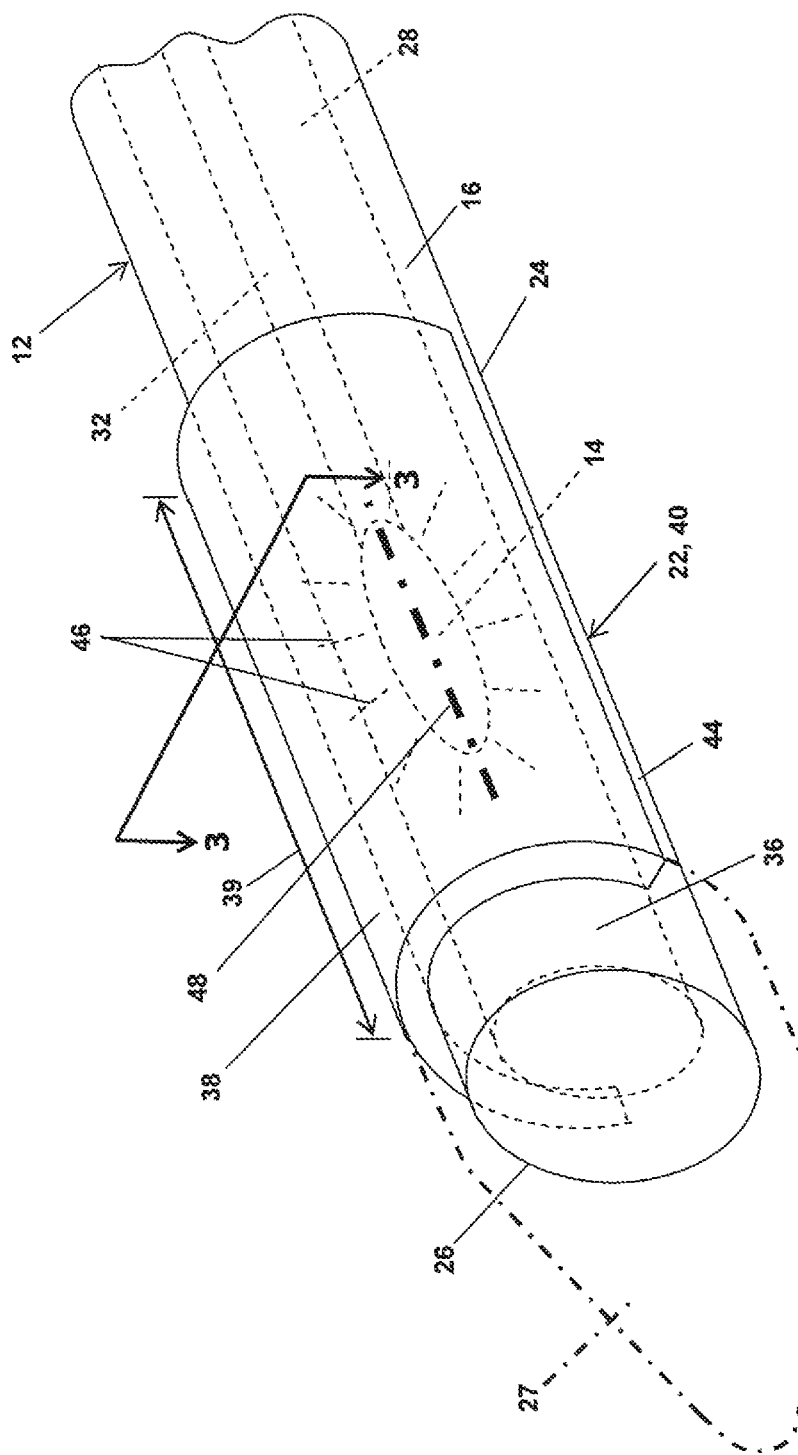
FIG. 2 is a perspective view of a catheter according to an embodiment of the invention.
Figure 4:
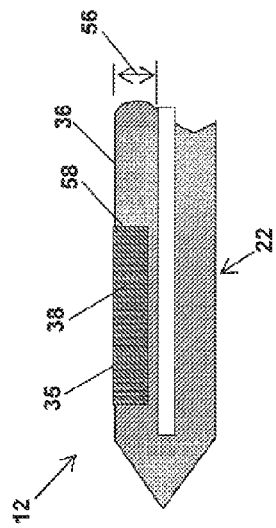
FIG. 4 depicts a distal end portion of an embodiment of an HDR catheter in cross-section.
Figure 5:
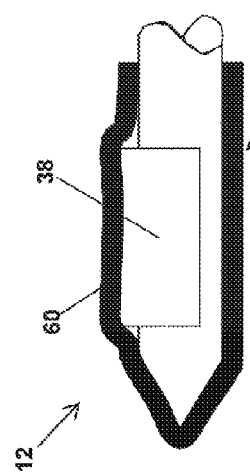
FIG. 5 is a cutaway view of a distal end portion of an embodiment of an HDR catheter.
Figure 3:
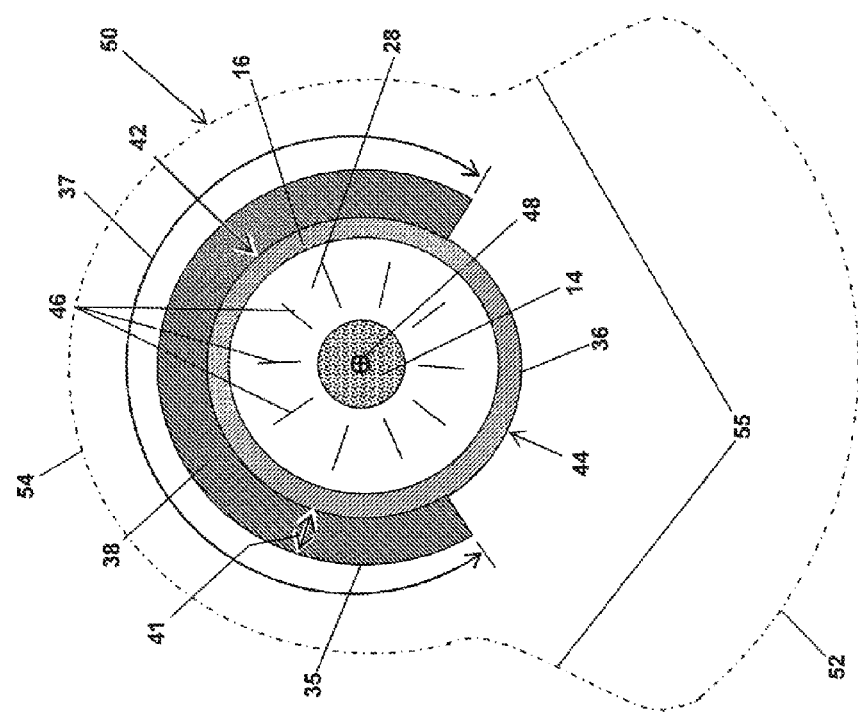
FIG. 3 is a cross-sectional view of the catheter of FIG. 1 taken at line 3-3 of FIG. 2.

Referring to FIGS. 1, 2 and 3, a high dose radiation delivery system 10 for an HDR catheter 12 with a retractable radiation source 14 is depicted. The HDR catheter 12 comprises a tubular element 16 having a central axis 17, a proximal end portion 18, a mid portion 20 and a distal end portion 22 having an outer peripheral surface 24 and a free end 26. The free end 26 may be formed or fitted with a tip portion or cutting member 27, as shown in phantom in FIG. 2 to aid in insertion of the HDR catheter 12. A lumen 28 passes through the proximal end portion 18, mid portion 20 and into the distal end portion 22 of the HDR catheter, terminating near the free end 26 of the distal end portion 22.

An afterloader 30, such as the microSelectron™ afterloader manufactured by Nucleotron Corp., is used to drive the radiation source 14 into and out of the lumen 28 by way of a drive wire 32. The afterloader 30 is connected to the proximal end portion 18 of the HDR catheter through a coupling 34 that readily disconnects from the HDR catheter. The coupling 34 may comprise a luer lock or a compression type fitting. The afterloader 30 is capable of placing the radiation source 14 into the distal end portion 22 of the HDR catheter.

The outer peripheral surface 24 defines an outer circumference or periphery 36 of the distal end portion 22 when viewed in cross-section (FIG. 3). In one embodiment, a radiation attenuator 38 having an outer radial surface 35, an arc length 37, an axial length 39 and a thickness 41 is disposed on a portion of the outer peripheral surface 24 of the distal end portion 22, covering only a portion of the outer periphery 36. The radiation attenuator 38 thus delineates a partially shrouded zone 40 of the distal end portion 22 of the HDR catheter having an attenuated portion 42 that is covered by the radiation attenuator 38 and a window portion 44 defined by the uncovered portion of the outer periphery 36. Preferably, the radiation attenuator 38 is made of a high density material such as lead or tungsten.

In operation, the afterloader 30 is connected to the HDR catheter, the radiation source 14 and the drive wire 32 are inserted into the lumen 28 at the proximal end portion 18 of the catheter, and the radiation source 14 is made to pass through the lumen 28 and to reside within the partially shrouded zone 40 of the distal end portion 22. The radiation source 14 emits radiation 46 having a substantially uniform radial intensity profile about a central axis 48 of the radiation source 14 which is approximately coincident with the central axis 17 of the HDR catheter.

The presence of the radiation attenuator 38 creates a non-uniform radiation intensity profile 50 about the central axes 48 and 17 when the radiation source 14 is lodged in the partially shrouded zone 40. A first or "unattenuated" portion 52 of the radiation intensity profile 50 passes through the window portion 44 of the partially shrouded zone 40 with little attenuation. A second or "attenuated" portion 54 of the radiation intensity profile 50 passes through the radiation attenuator 38, thereby reducing the intensity of the second portion 54 of the emitted radiation 46 as it passes therethrough. Generally, there is a transition portion 55 of the radiation intensity profile 50 at the confluence between the unattenuated and attenuated portions 52 and 54. The reduction in the intensity of the attenuated portion 54 of the emitted radiation 46 may be tailored by fabricating the radiation attenuator 38 from a material having an appropriate linear or mass attenuation coefficient, or by altering the thickness 41 of the radiation attenuator 38, or some combination thereof. Moreover, the directional characteristics of emitted radiation 46 may be modified by altering the arc length 37 of the radiation attenuator 38.

Accordingly, the radiation profile exiting the partially shrouded zone 40 of the HDR catheter can be tailored for significant reduction in the intensity of the attenuated portion 54, enabling the catheter to deliver high doses of radiation in the direction of malignant tissue while significantly reducing the exposure of neighboring healthy tissue and organs.

Referring to FIGS. 4, 5, 6 and 7, other embodiments of the invention are presented. The embodiment depicted in FIG. 4 portrays an HDR catheter 12 with a wall thickness 56 thick enough to accommodate an inset 58 in the distal end portion 22 of the HDR catheter 12 that accepts the radiation attenuator 38 so that the outer radial surface 35 of the radiation attenuator 38 is flush with the outer circumference 36 of the HDR catheter 12. The embodiment of FIG. 5 portrays the distal end portion 22 encapsulated in a shrink fit wrapper 60. The FIGS. 6 and 7 illustrations depict the distal end portion 22 of an HDR catheter 12 including a radiation attenuator 62 having transitional surfaces 64 and 66 and a lunately shaped cross-section 68.

Functionally, the embodiments presented in FIGS. 4, 5, 6 and 7 mitigate against damage to intervening tissue along the insertion path (not depicted) of the HDR catheter 12. The flush relationship between the outer radial surface 35 of the radiation attenuator 38 and the outer circumference 36 of the HDR catheter 12 creates an essentially smooth surface that enables the intervening tissue material to part over the distal end portion 22 during insertion, removal and rotation of the HDR catheter 12 with less resistance and less damage to the neighboring or intervening tissue. Likewise, the shrink fit wrapper 60 provides a smooth, soft surface that enables a smooth parting of intervening tissue. The shrink fit wrapper 60 provides the additional advantage of isolating the radiation attenuator 38 from contacting the body tissue, thereby reducing toxicological concerns that contact with certain materials (e.g. lead) may pose. The transitional surfaces 64 and 66 and the lunately shaped cross-section 68 of the embodiments illustrate in FIGS. 6 and 7 provide a similar functionality. The varying thickness across the arc length 37 of the lunately shaped cross-section 68 will also create a non-uniform attenuated radiation intensity 70 that may be desirable in certain instances. Other means that enable an exterior mounting of a radiation attenuator to an HDR catheter while mitigating the effects of abrupt surface transitions may also be utilized and will be apparent to those skilled in the art by virtue of this disclosure.

Figure 9:
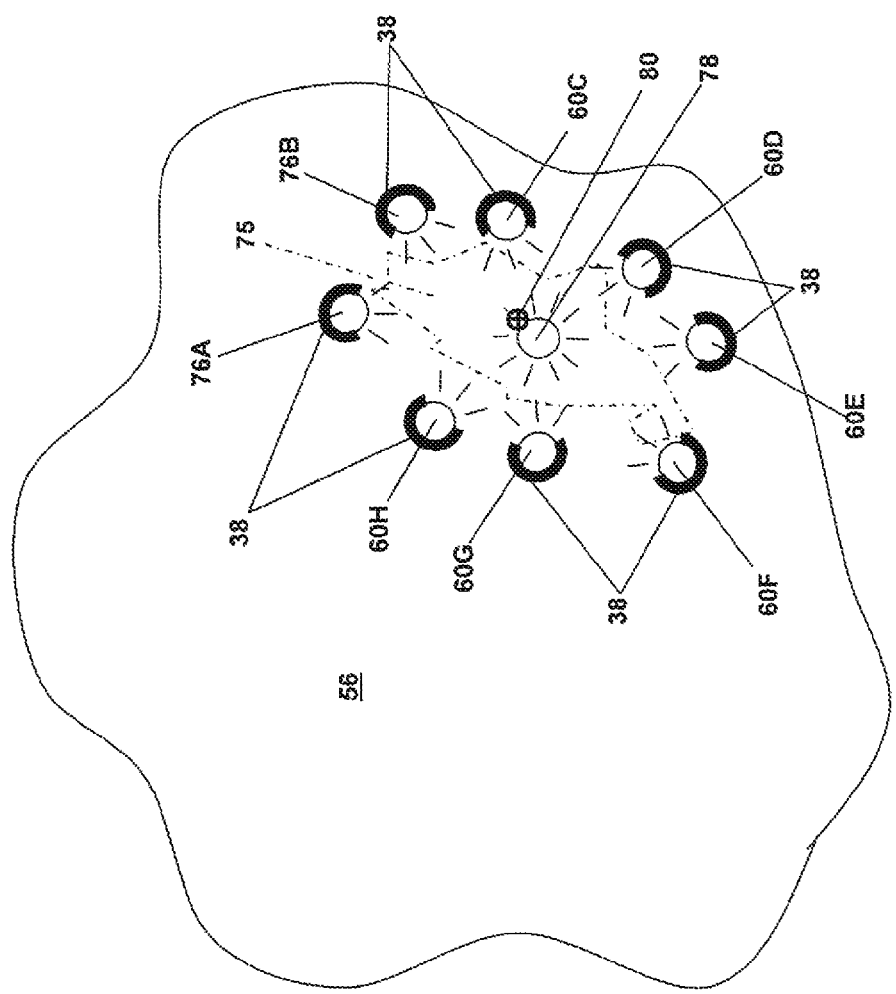
FIG. 9 is a cross-sectional view of a tissue mass under treatment of unifocal cancer according to an embodiment of the invention.

Referring to FIGS. 8 and 9, a method of using a plurality of the catheters 12 is described for the treatment of a tissue mass or gland 72 such as a prostate, breast, lung, esophagus or bile duct, anorectal and sarcoma having a center of mass 74. Some cancers, such as prostate cancer, tend to be "multi-focal" in nature, and are typically but not always characterized by cancerous cells dispersed throughout an affected region. Other cancers, such as breast cancer, tend to be "unifocal" in nature; these cancers may be characterized by a cancerous zone, depicted in phantom by numerical reference 75 in FIG. 9 that is to some extent delineated from healthy, non-cancerous tissues.

The treatment of a "multi focal" cancer is depicted in FIG. 8. A plurality of partially attenuated catheters 76A-76H, each fabricated in accordance with the aforementioned embodiments of the present invention. Each of the catheters 76A-76H is fitted with a radiation attenuator 38. The partially attenuated catheters 76A-76H are inserted into the tissue mass 72 and each is rotationally oriented so the respective window portion 44 faces toward the center of mass 74 of the tissue mass 72. The rotational orientation of a given partially attenuated catheter 76A-76H may be made before or after insertion into the tissue mass 72. An unattenuated catheter 78 having no radiation attenuator is also inserted into the tissue mass 72 in or near proximity to the center of mass 74, or in an area that may require a higher radiation dosage.

Once the tissue mass 72 is configured with the catheters 76A-76H and 78 as depicted, a method of treatment of the tissue mass 72 is as follows (with reference back to FIGS. 1, 2 and 3): The afterloader 30 is coupled to catheter 76A and the radiation source 14 and the drive wire 32 are inserted into the lumen 28 at the proximal end portion 18 of the catheter 76A. The radiation source 14 is pushed through the lumen 28 with the guide wire 32 and positioned so that it resides within the partially shrouded zone 40 of the distal end portion 22 of the catheter 76A. The radiation source 14 remains within the partially shrouded zone 40 for a predetermined dwell period of time before being retracted from the lumen 28 with the guide wire 32. Once the radiation source 14 is within the afterloader 30, the afterloader 30 is disconnected from the partially attenuated catheter 76A. This process may be repeated for some or all of the remaining catheters 76B-76H and 78.

Operationally, the orientation of the attenuators 38 in FIG. 8 reduces the intensity of radiation that irradiates neighboring regions of the tissue mass 56 while irradiating the multifocal cancerous member with a substantially uniform dosage of radiation. Preferably, the radiation source 14 is passed through the lumen 28 with expediency to limit exposure of healthy tissue and organs located adjacent the catheters 76A-76H and 78. The dwell period that the radiation source 14 spends in the partially shrouded zone 40 of a given catheter 76A-76H, 78 may be tailored to the dosage requirement of for the particular zone being irradiated.

The treatment of a unifocal cancer is depicted in FIG. 9. The HDR catheters 76A-76H are inserted into the tissue mass or gland 72, but are located in a more concentrated manner near the cancerous zone 75. The catheters 76A-76H are rotationally oriented to direct unattenuated radiation toward a center of mass 80 of the cancerous zone 75. Again, an unattenuated HDR catheter may be placed within the tissue mass or gland 72, preferably at or near the center of mass 80 the cancerous zone 75.

Operationally, the orientation of the attenuators 38 in FIG. 9 also reduces the intensity of radiation that irradiates the regions neighboring the tissue mass 56, as well as the healthy, non-cancerous tissues of the tissue mass 56 itself, while irradiating the unifocal cancerous zone 75 with a substantially concentrated dosage of radiation. Again, the radiation source 14 is preferably passed through the lumen 28 with expediency to limit exposure of healthy tissue and organs located adjacent the catheters 76A-76H and 78. The dwell period that the radiation source 14 spends in the partially shrouded zone 40 of a given catheter 76A-76H, 78 may be tailored to the dosage requirement of for the particular zone being irradiated.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

What is claimed is:

1. A method for selectively exposing portions of a tissue mass to radiation comprising:
   providing a plurality of partially attenuated catheters and at least one unattenuated catheter, each partially attenuated and unattenuated catheter comprising a hollow tubular element having a central axis and a distal end portion with an outer periphery, each partially attenuated catheter further including a radiation attenuator partially covering said outer periphery of said distal end portion, wherein said radiation attenuator defines an unattenuated window portion of said distal end;
   positioning each of said partially attenuated catheters into a tissue mass such that the unattenuated window portion faces a center of mass;
   positioning the at least one unattenuated catheter proximate the center of mass;
   inserting a radiation source through the hollow tubular element of one of said partially attenuated catheters such that the radiation source resides proximate the unattenuated window portion;
   withdrawing said radiation source from the partially attenuated catheter following a predetermined dwell period at the window portion;
   repeating the steps of inserting and withdrawing the radiation source for each remaining partially attenuated catheter positioned in the tissue mass;
   inserting the radiation source through the at least one unattenuated catheter; and
   withdrawing said radiation source from the at least one unattenuated catheter.

2. The method of claim 1, wherein the steps of inserting the radiation source comprises connecting a coupling on a proximal end portion of the hollow tubular element to an afterloader and delivering the radiation source with a drive wire passed through the hollow tubular element.

3. The method of claim 1, wherein the tissue mass comprises a multi-focal tissue mass.

4. The method of claim 1, wherein the tissue mass comprises a unifocal tissue mass.

5. A system for selectively treating a cancerous tissue mass comprising:
   an afterloader having a radiation source and a drive wire; and
   a plurality of high dose radiation catheters, each catheter comprising a hollow tubular element having a central axis, a proximal end portion, a mid portion and a distal end portion with an outer periphery, the proximal end portion including a coupling for attaching to the afterloader and the distal end portion including an inset for mounting a radiation attenuator, said radiation attenuator being covered by a shrink-wrapper positioned over the distal end portion, the radiation attenuator partially covering said outer periphery of said distal end portion so as to define a partially shrouded zone and a window portion;

wherein the plurality of high dose radiation catheters are adapted for individual insertion into a cancerous tissue mass such that the high dose radiation catheters surround a center mass with the window portion facing the center mass; and wherein the afterloader sequentially loads each high dose radiation catheter by positioning the radiation source at the distal end portion for a predetermined dwell time.

6. A system for selectively treating a cancerous tissue mass comprising:

an afterloader having a radiation source and a drive wire; and a plurality of high dose radiation catheters, each catheter comprising a hollow tubular element having a central axis, a proximal end portion, a mid portion and a distal end portion with an outer periphery, the proximal end portion including a coupling for attaching to the afterloader and the distal end portion including an inset for mounting a radiation attenuator, said radiation attenuator partially covering said outer periphery of said distal end portion so as to define a partially shrouded zone and a window portion, said radiation attenuator having a non-uniform cross-section defined by a plurality of transitional surfaces so as to define a non-uniform attenuated radiation intensity;

wherein the plurality of high dose radiation catheters are adapted for individual insertion into a cancerous tissue mass such that the high dose radiation catheters surround a center mass with the window portion facing the center mass; and wherein the afterloader sequentially loads each high dose radiation catheter by positioning the radiation source at the distal end portion for a predetermined dwell time.

7. The system of claim 6, wherein the non-uniform cross-section is lunately shaped.

* * * * *